United States Patent [19]

Okada

[11] Patent Number: 4,660,982
[45] Date of Patent: Apr. 28, 1987

[54] ADAPTOR FOR MEASURING LENGTH OPTICALLY FOR ENDOSCOPE

[75] Inventor: Minoru Okada, Hachioji, Japan

[73] Assignee: Olympus Optical Co., Ltd., Tokyo, Japan

[21] Appl. No.: 731,644

[22] Filed: May 7, 1985

[30] Foreign Application Priority Data

May 9, 1984 [JP] Japan ................................ 59-93798

[51] Int. Cl.⁴ .............................................. G01B 11/02
[52] U.S. Cl. ........................................ 356/383; 128/6
[58] Field of Search ...................... 356/383, 384, 241; 128/4, 6, 7, 8, 9, 303.15, 634

[56] References Cited

U.S. PATENT DOCUMENTS

| 3,817,631 | 6/1974 | Kawahara | 356/1 |
| 3,817,635 | 6/1974 | Kawahara | 356/11 |
| 4,271,829 | 6/1981 | Heckele | 356/383 |
| 4,588,294 | 5/1986 | Siegmund | 356/241 |

FOREIGN PATENT DOCUMENTS

| 5568110 | 11/1953 | Japan . | |
| 51-45911 | 12/1976 | Japan . | |
| 5380284 | 12/1976 | Japan . | |
| 53-80285 | 7/1978 | Japan . | |
| 145832 | 11/1981 | Japan . | |
| 57-54004 | 11/1982 | Japan . | |
| 0060719 | 4/1983 | Japan | 356/383 |
| 0060720 | 4/1983 | Japan | 356/383 |
| 0072117 | 4/1983 | Japan | 356/383 |
| 1132906 | 1/1985 | U.S.S.R. | 128/6 |

Primary Examiner—F. L. Evans
Attorney, Agent, or Firm—Armstrong, Nikaido, Marmelstein & Kubovcik

[57] ABSTRACT

An optical adaptor incorporating a projecting optical system, view field-changing optical system and at least one index attached to said projecting optical system is provided to be attached detachably to the tip portion of insert member of an endoscope equipped with an illuminating optical system for illuminating an object and an objective optical system for focusing the object into the elongated tip of the insert member, thereby enabling measuring the length of the object by projecting the index to the plane including the object.

7 Claims, 25 Drawing Figures

ADAPTOR FOR MEASURING LENGTH OPTICALLY FOR ENDOSCOPE

FIELD OF THE INVENTION AND RELATED ART STATEMENT

This invention relates to an adaptor for measuring optically the size of an object to be observed, the adaptor being detachably connected to the tip of the main body of an endoscope.

Endoscopes have been employed widely in therapeutical and industrial fields.

In order to diagnose, for example, a diseased portion developed on the inner wall of stomach or to examine the change of such a diseased portion with time, it is frequently necessary to measure the size of the diseased portion or to know the distance to the diseased portion while observing through an endoscope.

When a distance to a portion or object to be tested, such as a diseased portion or a size from the visual field is to be estimated by a conventional endoscope or an endoscope for measuring length, such a distance or size has been detected from the adjusted amount of displacement when the focus of the observing optical system has been adjusted. Due to the inherent optical system in the endoscope, lenses having a large depth are employed and the object to be examined has poor change in the colors or patterns, so that precise adjustment of the focus is difficult in such a case. Additionally, the precise measurement of length of the object required for the diagnosis cannot be achieved.

As known, a length-measuring endoscope as disclosed in Japanese Patent Publication No. 45911/1976 is designed so as to project a spot of light on to the object through a projector arranged at the tip side of the insert member so that the light is crossed at a large angle with the optical axis of the objective lens system. A scale graduated along the direction of displacement of the spot of light is arranged corresponding to the distance to the object at the vicinity of the focal plane of the eyepiece lens, thereby enabling measuring of the distance or the like from the graduations corresponding to the position of the spot within the visual field. However, this prior art has the disadvantage that since the means for projecting the spot of light for measuring a length is attached undetachably at the tip of the insert member thereby extending the length of the hard tip portion of the endoscope, the patient is forced to put up with severe pain during the insertion of the hard tip through the body cavity even when length measurement is not required.

The prior art has also a disadvantage that another exclusive length-measuring endoscope is required when the length-measuring observation is required at a different field angles. This increases markedly the economical burden on health care providers.

An endoscope as disclosed in Published Japanese Patent Application No. 80284/1978 has an optical system for projecting an index light together with a normal observation optical system and illuminating optical system. This is disadvantageous in that the endoscope has a complicated structure, thus, increasing manufacturing costs. Further, increasing the outer diameter of the insert member and extending the rigid tip of the insert member results in the patient suffering severe pain during the insertion of the insert member even when the length-measurement is not performed. It is also disadvantageous similarly to the above-mentioned prior art in that when the observation measuring the length at a different direction of visual field is required, another exclusive endoscope is required which increases very much the economical burden on health care providers and ultimately the patients.

An endoscope as disclosed in Published Japanese Patent Application No. 80285/1978 employs a spot light having a discriminative color but has otherwise substantially similar disadvantages to above-mentioned prior arts.

Japanese Utility Model Publication No. 54004/1982 proposes a length-measuring instrument wherein the light is irradiated from the side of the a fiber lens of light converging type of changing the ion concentration from the radial centre of a glass column to the periphery thereof to reduce the refraction index gradually from the central side to the surface and utilizing light issued radially as the datum line. In addition, Published Japanese Utility Model Application No. 68110/1980 discloses an endoscope employing such a length-measuring instrument.

This prior art endoscope is provided with a normal observation optical system and illuminating optical system at the tip side of the insert member. The light converging lens which is irradiated with laser light transmitted through a light converging system to the tip side on the side thereof causes light to issue radially from the light-converging lens which is reflected, in turn, by a conical mirror to project and display a circle having a datum circle on the objective side.

Since this prior art is also attached undetachably at the tip of insert member similarly to above-mentioned prior arts, it has a disadvantage that the patient is forced to suffer from pain during the insertion into or removal from the body cavity even when the length-measurement is not carried out. Moreover, when the length-measurement is performed at a different angle of field, another length-measuring endoscope is required. Furthermore, when it is applied to a directly observing type endoscope for observing in the forward axial direction of the insert member, the diameter of insert member is increased to limit the site to be observed or operated upon.

Furthermore, in published Japanese Patent Application No. 145832,1981, there is arranged an optical fibre for projecting a target light at a constant distance from the optical fibre for transmitting an image to project target light from the issuing end of the optical fibre to the object side at a constant angle with the optical axis of the optical fibre for transmitting image to measure the distance from the tip of insert member to the object from the position of target light image within the visual field.

This prior art is designed to prevent any accidental injury of the object to be observed by the tip of insert member of endoscope so that it has a disadvantage that the size of diseased portion can substantially not be grasped during the observation.

Moreover, when it is employed for measuring the size of diseased portion, there occurs a problem that the required accuracy cannot be achieved easily over a wide range of observable distances by single spot light.

OBJECTS AND SUMMARY OF THE INVENTION

It is an object of this invention to provide an optical adaptor for measuring a length for an endoscope capable of measuring length by attaching the adaptor to the endoscope.

It is another object of this invention to provide an optical adaptor for measuring a length for an endoscope that is capable of measuring the length at a different angles of field or a different direction of the visual field.

It is still another object of this invention to provide an optical adaptor for measuring a length for an endoscope capable of forming a datum index suitable for measuring length.

It is still further object of this invention to provide an optical adaptor for measuring a length for an endoscope capable for measuring the length while lower costs.

It is still a further object of this invention to provide an adaptor which can be inserted easily by reducing the length of the rigid tip of inset member of the endoscope when no length-measurement is required.

This invention realizes a length-measurable endoscope capable of changing the visual field by incorporating a projecting optical system provided with an index and visual field-variable optical system to an optical adaptor provided with detachably attaching means at the tip of insert member of endoscope.

Other features and merits of this invention will become obvious by the following description:

BRIEF DESCRIPTION OF THE DRAWINGS

FIGS. 1 to 6 relate to a first embodiment of this invention, wherein

FIGS. 8 to 10 relate to a third embodiment of this invention, wherein

FIGS. 11 to 14 relate to a fourth embodiment of this invention, wherein

FIGS. 15 to 17 relate to a fifth embodiment of this invention, wherein

FIGS. 18 to 20 relate to a sixth embodiment of this invention, wherein

FIGS. 21 to 23 relate to a seventh embodiment of this invention, wherein

DETAILED DESCRIPTION OF PREFERRED EMBODIMENTS

Figures 1, 2:
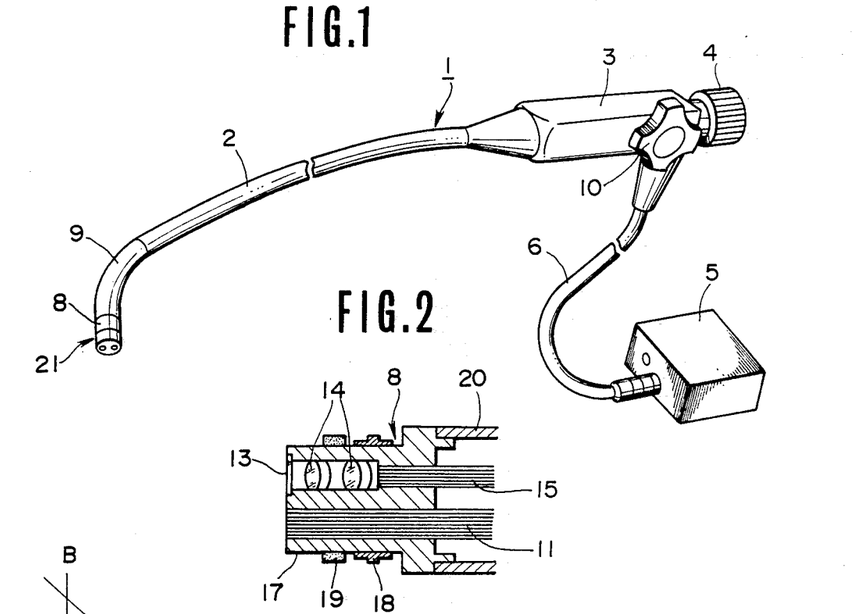
FIG. 1 is a perspective view of endoscope having the first embodiment.
FIG. 2 is an enlarged longitudinal sectional view of the structure of the tip of the insert member of the endoscope.

As shown in FIG. 1, an endoscope 1 having detachably attached hereto the first embodiment 21 of the present invention comprises an elongated and flexible insert member 2 for inserting into a body cavity or the like, a handle member 3 connected to the trailing end of the insert member 2 and having a larger diameter, an eyepiece member 4 attached at the trailing end of the handle member 3, and a flexible universal cord or light guide cable 6 extended outwards from the side of handle member 3 and a connecting connector at the end of handle member 3 and attachable to light source means 5.

As shown in FIG. 1, rigid tip member 8 incorporated with observation means and illuminating means is connected to a bend member 9 adjacent to the trailing end of the tip member 8. Means (not shown) are connected successively to the tip of said insert member so as to bend the bend member 9 horizontally or vertically by turning knob 10 attached to the handle member 3.

A light guide 11 formed from a flexible optical fibre bundle for transmitting illuminating light is inserted through the universal cord 6 and insert member 2. The light guide 11 transmits light irradiated on one end surface of light source means 5 from an illuminating lamp (not shown) and projects the light from the tip surface attached fixed at tip member 8 as shown in FIG. 2 onto an object in front of the tip surface for illuminating the object.

Tip member 8 attached fixedly the tip of the light guide 11 has a first through-hole provided for the light guide 11, and a second through-hole provided, for example, at a position above the first through-hole in parallel thereto. The second through-hole is closed with a cover glass 13. An objective optical system 14 is attached in the tip member 8 behind the cover glass as an observation means. The leading tip of image guide 15 formed of an optical fibre bundle is attached fixedly to tip member 8 so that the leading surface thereof is positioned at the focal plane of the objective optical system 14 for transmitting the image focused on the leading surface to the eyepiece member 4 so as to be observed through eyepiece lens 16 of eyepiece member 4 as shown in FIG. 3.

The outer periphery of the tip member 8 is stepped to a smaller diameter at the leading portion than that at the vicinity of trailing end thereof. A stopper ring 18 provided with a protrusion ring therearound for engaging the first embodiment of the present invention is fixedly attached to the outer periphery of portion 17 stepped to the smaller diameter. An elastic ring 19 functioning as a water-tight sealing member is also fixedly attached at a more forward adjacent position. The outer periphery of trailing end of tip member 8 is also attached fixedly with the leading end of flexible sheath tube 20. An articulated train (not shown) is incorporated within said sheath tube having an appropriate length and is attached adjacent to the tip member 8 for forming the bend member 9.

Figure 3:
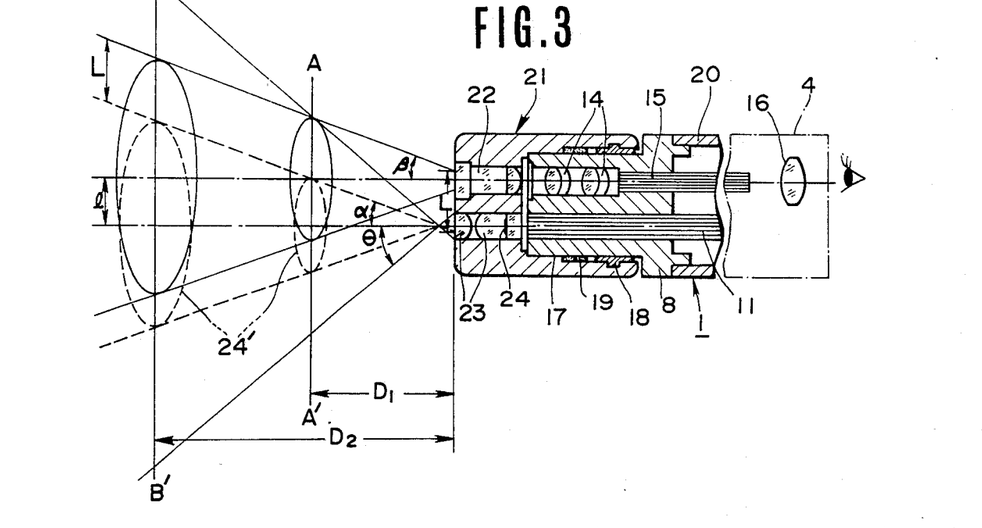
FIG. 3 is a schematic view showing the projecting optical system and focusing optical system when the first embodiment is attached to the tip of the endoscope.

In addition, a length-measuring optical adaptor 21 of the first embodiment is attached detachably through the outer periphery of the tip member as shown in FIG. 3.

The length-measuring adaptor 21 includes a body formed with a bore to be fitted on the outer periphery of portion 17 having the smaller diameter at the vicinity of trailing end of the tip member 8. The inner periphery of trailing end side of the bore mates with stopper ring 18 and is provided with an annular recess or groove for engaging the protrusion around the stopper ring 18. Additionally, the inner periphery of the bore pressure-fits with elastic ring 19 at the vicinity of said stopper ring 18 to seal the outer periphery of portion 17 with the inner periphery of the bore to assure water-tightness.

Figures 4A, 4B:
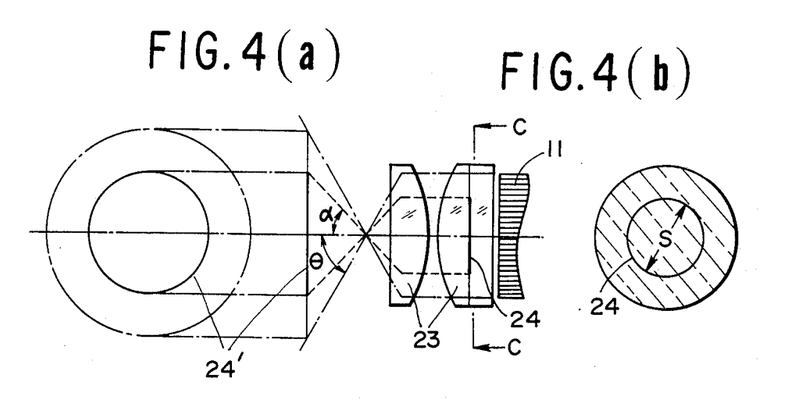
FIG. 4(a) is a schematic view illustrating portionwise the projecting optical system.
FIG. 4(b) is a sectional view taken along line C—C in FIG. 4(a)

A visual field changing optical system 22 is inserted in a first through hole provided through the length-measuring optical adaptor at a position confronting the objective optical system 14 incorporated within tip member 8 when the adaptor is attached to tip member 8. In addition, a projecting optical system 23 is inserted in a second through hole provided at the position confronting the leading tip of light guide 11. A circular index 24 having a diameter of S as shown in FIGS. 4(a) and (b) is formed around the optical axis of projecting optical system 23 at the position outward to the focal distance f of the projecting optical system, and preferably at the position focusing the index at a distance of 5 to 50 mm from the objective. The circular index is designed to be projected forwards in concentrical cone having an apex with an angle inclined from the optical axis at an angle of $\alpha$ within the conical angular illuminating range having an apex with an angle inclined from the optical axis at an angle of $\theta$ by the projecting optical system 23 as shown in FIG. 3 or FIG. 4(a).

An object in front of the adaptor within the angular focusing range defined by a cone inclined from the optical axis at an angle of $\beta$ can be focused at the leading end of image guide 15 by the focusing optical system comprising the visual field changing optical system 22 and the objective optical system 14. In addition, the optical axes of the visual field-changing optical system 22 and the projecting optical system 23 are designed to be in parallel to each other and apart by a constant distance l with respect to each other.

Since the focusing angular range $\beta$ is set to be equal to the projecting angle $\alpha$ of index 24, the distance defined by the uppermost point of visual field of circular focusing range or the observation range and the uppermost point of arc of projected index 24 is kept at a constant value irrespective of the object viewed as shown by line A—A' spaced from the leading end of length-measuring optical adaptor by a distance $D_1$ or as shown by line B—B' spaced from the adaptor by a distance $D_2$ as shown in FIG. 3. In other words, if the distance between the heights of light of index 24 on the first lens plane of the projecting optical system 23 is assumed to be L as shown in FIG. 3, then the value L is a constant irrespective of the distance to the object being viewed.

In the first embodiment, datum length displaying means are formed by providing a datum length of L on the side of the object desired to be measured for length. (In addition, the surface of object for forming the image of circular index by means of projecting optical system 23 is shown as being inclined relative to a plane perpendicular to the drawing for convenience in FIG. 3. In other embodiments, the image of index may be provided at an incline.) Hence, when the object on line A—A' or B—B' is observed through eyepiece member 4 as shown in FIG. 3, a portion of the image of the index as represented by numeral 24" is focused, the image of the index projected on the surface of the object as represented by numeral 24' is observed as shown by broken line in FIGS. 5 or 6. The length from the uppermost point of visual field and the uppermost point of the arc of the image of the index 24" corresponds to the datum length L.

Accordingly, a size or length of an object within the observing visual field can be estimated easily from the constant and correct length displayed within the visual field or estimated more accurately by utilizing photography or the like.

In addition, distance D to the object can be calculated from an equation:

$$R/(D-f)=S/2f$$

or $$D=f(2R+S)/S$$

wherein the radius of index 24' projected on the object surface at a distance of D is assumed to be R. (S is the actual diameter of the circular index 24 and f is the focal distance of the projecting optical system 23). When $R>>S$, then $$D=2fR/S$$

and R can be calculated from the datum length L.

The operation of first embodiment having a structure as stated hereinabove is as follows:

When the bore of the length-measuring optical adaptor 21 according to the first embodiment is fitted onto portion 17 having a smaller diameter of tip member 8 of endoscope 1 and pressed, the protruded ring of stopper member 18 is received in the ring groove provided around the inner periphery of the bore of the adaptor 21 to engage the adaptor with the tip member. The length-measuring adaptor 21 engaged with the tip member is inserted, for example, from the oral cavity through the body cavity to the position confronting the object to be examined and the object is observed at a distance suitable for the observation. In such a case, the illuminating light from the illuminating lamp (not shown) in light source means 5 is transmitted through light guide 11 and irradiated from the leading end of light guide through projecting optical system 23 within the range of illuminating angle θ. Index 24 is projected through projecting optical system 23 on the surface of object in a circular form at an angle of α.

Figure 5:
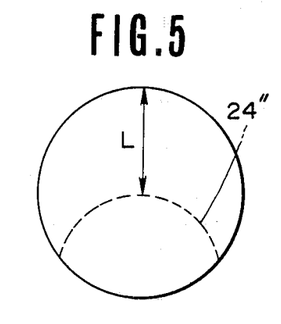
FIG. 5 is a schematic view illustrating the image of an index observed from the eyepiece member and FIG. 6 is a schematic view illustrating the image of the index observed from the eyepiece member when the projecting light is projected on an object present farther than that in FIG. 5.
Figure 6:
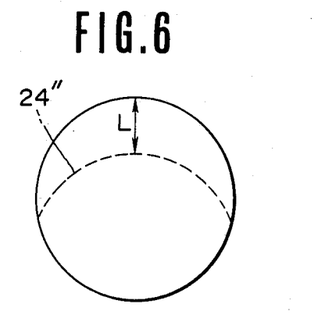

Since angle β of the field of the focusing optical system is equal to the angle α, a portion of the image 24" for the projected index 24' is observed together with the illumination by the illuminating optical system as shown in FIGS. 5 or 6. Since the length from the uppermost point of visual field to the uppermost point of the image of the index 24" projected within the visual field corresponds to constant datum length L, the length of diseased portion or the like within the observing visual field can be estimated from the datum length L substantially irrespective of distance D to the object and can be more accurately determined from photographs taken through the endoscope.

As set forth hereinbefore, distance D to the objective can be calculated from the equation of $$D = f(2R + S)/S.$$

Moreover, according to this first embodiment, the projected image forms an arc, so that if a portion is not discriminated easily, it can be calculated from other distinct portions by extrapolation. The distance and size of the object viewed can be always estimated to help very much in the diagnosis and observation.

Still more, when the length is not required to be measured, the endoscope can be employed in a similar manner to a conventional endoscope by detaching the length-measuring optical adaptor 21. Since the length of rigid tip portion can be reduced to that of tip member 8, the pain experienced by a patient can be mitigated during the insertion of tip member through the body cavity of patient. The illumination can be increased by elimination of the loss in the intensity of illuminating light previously caused by index 24. Still further, when the endoscope is employed by detaching the length-measuring optical adaptor, it is preferred to attach a ring cover around the outer periphery of portion 17 having reduced diameter so that stopper member is 18 kept out of the way during the insertion and removal of the tip member of the endoscope.

Figure 7:
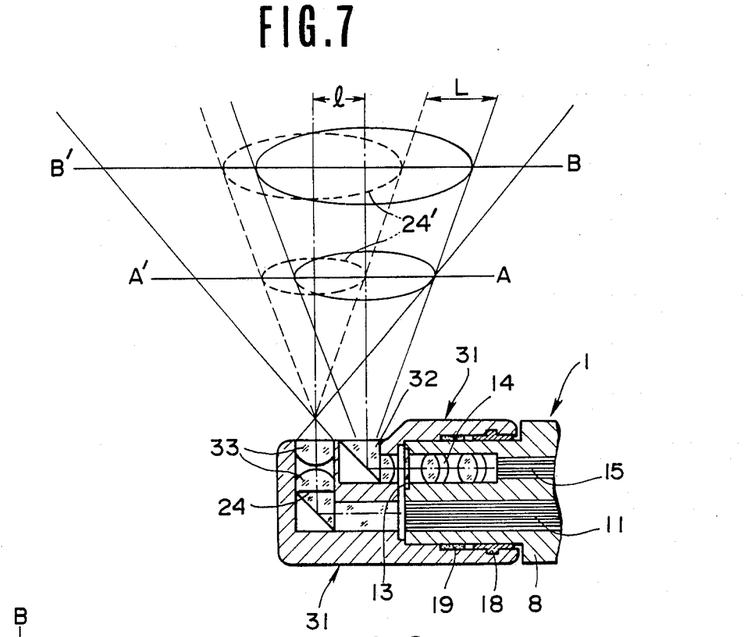
FIG. 7 is a schematic view of a second embodiment of this invention.

FIG. 7 illustrates the second embodiment of this invention.

In length-measuring optical adaptor 31 according to the second embodiment, two through holes are provided so that the trailing ends thereof confront respectively the leading ends of the objective optical system 14 and the light guide 11. The holes are bent through a right angle midway to open through the side of the adaptor. The through-holes are provided respectively with a visual field-changing optical system 32 and a projecting optical system 33, each attached optically with prisms. Circular index 24 is provided at the rear side of the projecting optical system 33. This second embodiment is only different from the first embodiment of a directly forward viewing type relative to the axial direction of tip member 8 in that it is a side-viewing type to the direction perpendicular to the axial direction of tip member 8 so that the same members corresponding to those of the first embodiment are represented by the same numerals. In addition, the function thereof is substantially equal to that of the first embodiment. Moreover, the distance between the both optical axes bent perpendicular to the side is represented by "l" and the distance between the height of angle of visual field and height of index is represented by datum length "L".

If the adaptors of first and second embodiments are provided, the directly forward and sideward visual fields can be observed under the length-measuring condition by employing a single endoscope. In addition, an adaptor having a different angle of field can be provided according to the first or second embodiment. Since these adaptors according to the first and second embodiments can be attached detachably to the same endoscope, such attachments can be realized with low costs.

Figure 8:
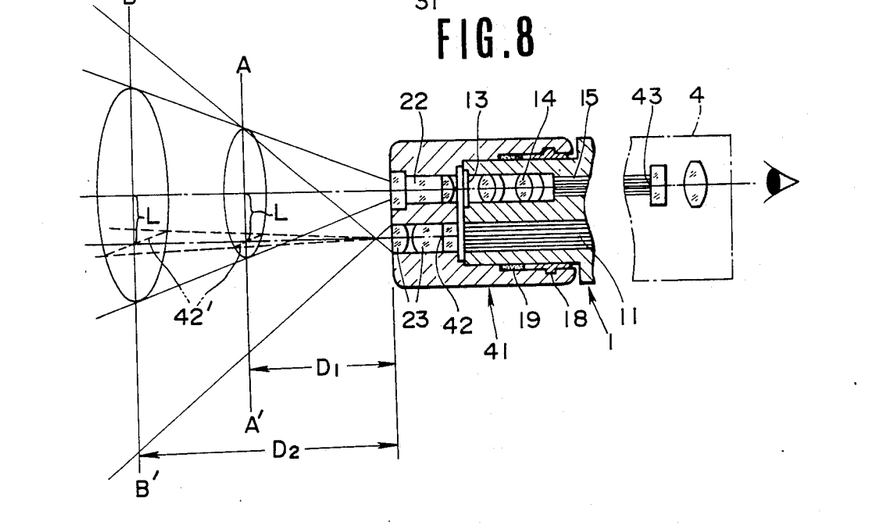
FIG. 8 is a schematic view of optical systems according to the third embodiment.

FIG. 8 illustrates the third embodiment of this invention. In the length-measuring optical adaptor 41 according to the third embodiment, linear index 42 is provided in lieu of the provision of circular index 24 as in the first embodiment so that the linear index 42 crosses the optical axis of projecting optical system 23 and is perpendicular to the plane including both optical axes of visual field-changing optical system 22 and projecting optical system 23. In addition, a datum index 43 is provided so that it passes the centre of visual field in parallel to projected index 42' of the linear index 42.

In such a structure, the projected index 42' is projected always so as to be parallel to the optical axis of visual field-changing optical system 22 or objective optical system 14 and to be aligned with the extended optical axis of projecting optical system 23. The distance between projected index 42' and the optical axis of visual angle-changing optical system 22 is kept always at a constant length L.

Figure 9:
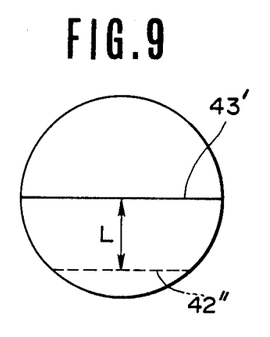
FIG. 9 is a schematic view illustrating the image of the index observed from the eyepiece member and FIG. 10 is a schematic view showing the image of the index observed from the eyepiece member when the projecting light is projected on an object present farther from the adaptor than the object in FIG. 9.
Figure 10:
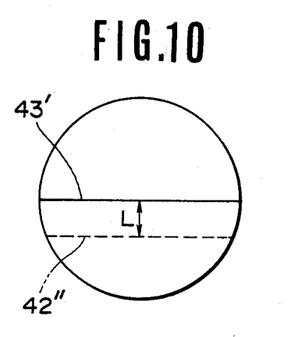

Consequently, when indexes 42', 42' projected on the surfaces of an object spaced from the leading end of adaptor by a distance $D_1$, $D_2$ are observed through eyepiece member 4, projected images of linear indexes 42", 42" are observed in parallel to the line of image 43' of the datum index 43 as shown in FIGS. 9 and 10. The distances between the two parallel lines are equal to datum length L in both cases. The effect thereof is substantially equal to that according to the first embodiment.

In addition, according to the third embodiment, the index is positioned at a constant point when an optical adaptor having different visual angle is manufactured, so that a common projecting optical system 22 can be utilizable to reduce the manufacturing costs.

Moreover, since datum length L is defined at the centre of visual field, it is easily seen and facilitates the measurement of length.

Still further, when the main body of endoscope is connected with a television camera, datum index 43 may be attached not to the endoscope but to the monitor display. By the way, the datum index 43 is not always necessary.

Figure 11:
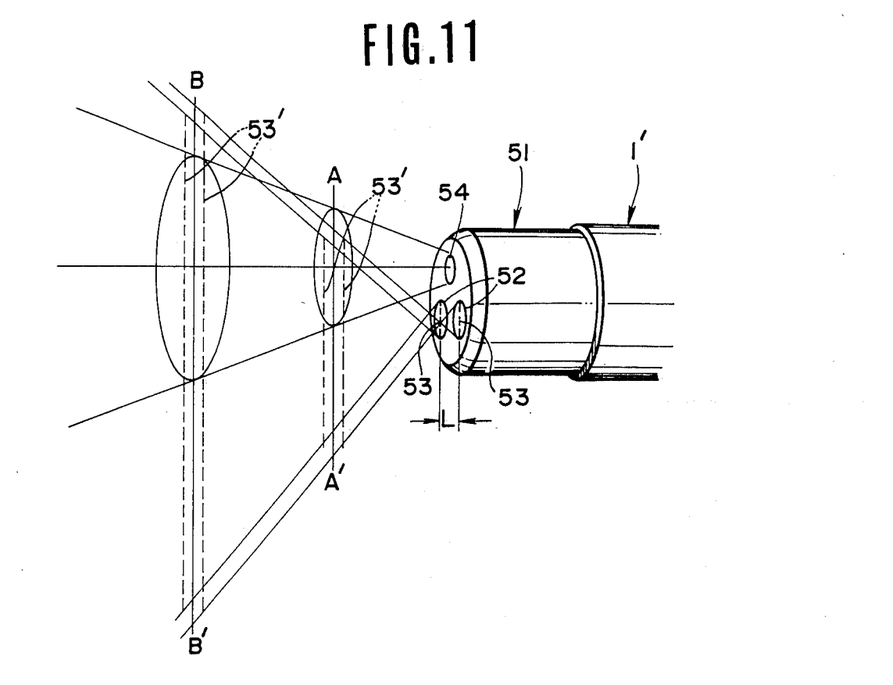
FIG. 11 is a perspective view of the fourth embodiment.

FIG. 11 illustrates the fourth embodiment of this invention.

Length-measuring optical adaptor 51 of the fourth embodiment is provided with two projecting optical systems. 52, 52.

Figures 12A, 12B:
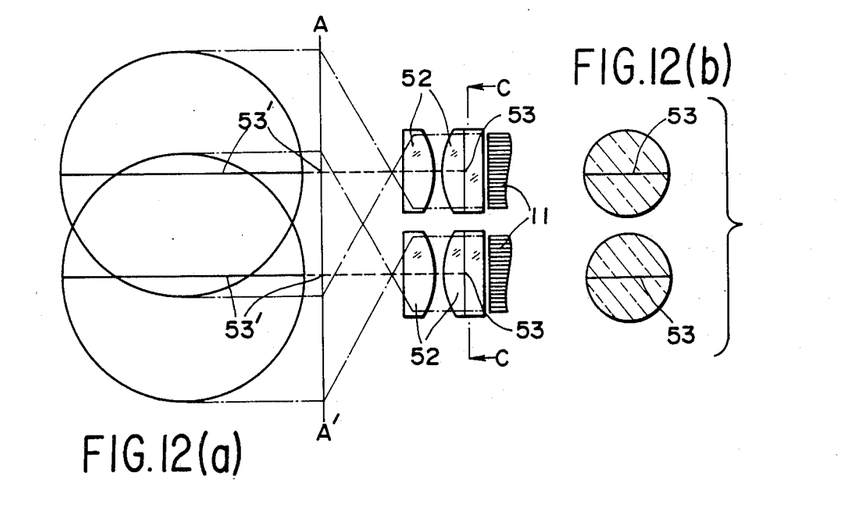
FIG. 12(a) is an enlarged schematic top view showing portionwise of the projecting optical system.
FIG. 12(b) is a sectional view taken along line C—C in FIG. 12(a)

Two light guides 11, 11 are arranged spaced apart at a central distance of L to each other, for example on the lower portion of the objective optical system of endoscope 1' to form an illuminating means as shown in FIG. 12. Through-holes are provided through the length-measuring optical adaptor 51 is confronting relation with the light guides 11, 11 and projecting optical systems 52, 52 are incorporated therein. As shown in FIGS. 11 and 12, linear indexes 53, 53 are provided so as to cross perpendicularly to a straight line connecting the optical axes of projecting optical systems 52, 52 and are parallel to each other. The distance between two indexes 53, 53 is kept always at a constant length of L (for example, 3 mm) and the distance of projected indexes 53', 53' are also kept at the length L.

Figure 13:
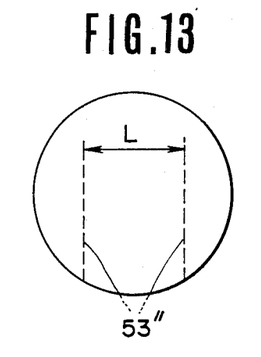
FIG. 13 is a schematic view illustrating the image of the index observed through the eyepiece member and FIG. 14 is a schematic view illustrating the image of the index observed through the eyepiece when the projecting light is projected on an object present farther from the adaptor than the object in FIG. 13.
Figure 14:
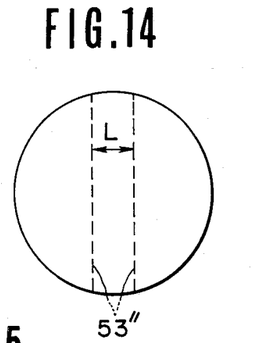

Consequently, when the image projected at line A—A' or lines B—B' as shown in FIG. 11 is observed through the eyepiece member, it is observed as shown in FIG. 13 or 14. The distance between the images of indexes 53", 53" is proved to be equal to the constant length L. In addition, the portion confronting the objective optical system of length-measuring adaptor 51 is provided with visual field changing optical system 54.

Since the fourth embodiment is provided with two illuminating optical systems, the illuminating light intensity is higher than that in a single illuminating optical system. Other effects are similar to that of the third embodiment.

Figure 15:
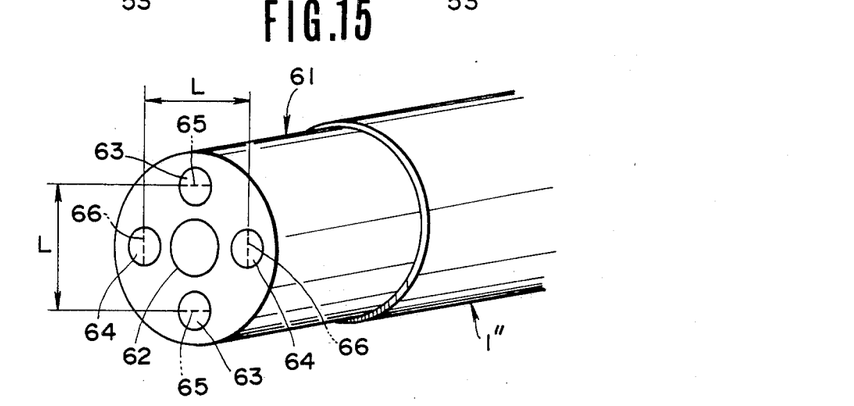
FIG. 15 is a perspective view according to the fifth embodiment of this invention.

FIG. 15 illustrates the fifth embodiment of this invention.

Length-measuring optical adaptor 61 according to the fifth embodiment is applied to an endoscope 1" provided with four illuminating optical systems.

Figure 16:
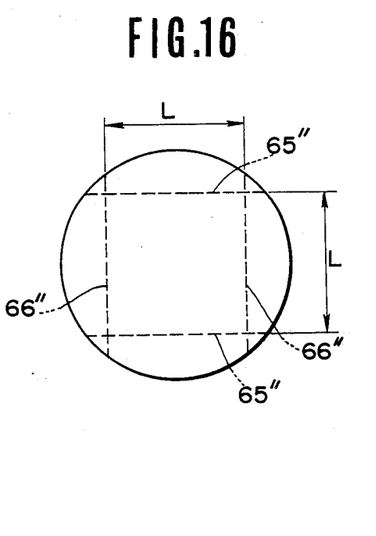
FIG. 16 is a schematic view of the image of the index observed through the eyepiece member and FIG. 17 is a schematic view of the image of the index observed through the eyepiece member when the projecting light is projected on an object present farther from the adaptor than the object in FIG. 16.
Figure 17:
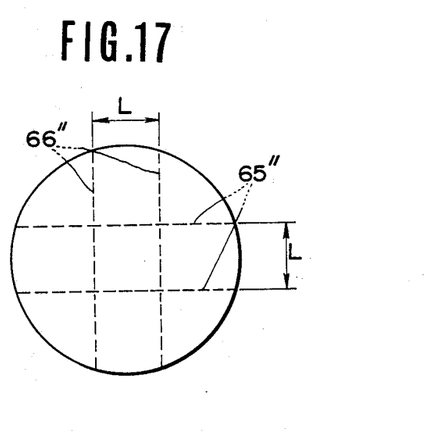

As shown in FIG. 15, visual field changing optical system 62 is provided at the centre and four projecting optical systems, 63, 63; 64, 64 are provided so as to be spaced apart from the visual field changing optical system 62 by an equal central distance of L/2 and to be symmetrical with respect to the optical axis of the visual field changing optical system 62. Two pairs of linear indexes 65, 65; 66, 66 are provided for each pair of projecting optical systems 63, 63; 64, 64 each in parallel. Hence, images of indexes 65", 65"; 66", 66" are observed within the visual field observed through the eyepiece member when the indexes are provided to a position relatively nearer from the adaptor as shown in FIG. 16 and images of indexes 65''', 65'''; 66''', 66''', are observed when the indexes are projected to a position relatively farther from the adaptor as shown in FIG. 17. The distances between a pair of images of the indexes 65", 65" and between another pair of images of the indexes 66", 66" are equal to a constant length L.

Other structure and functioning of the fifth embodiment are similar to those of first and second embodiments.

Since the datum length L is indicated concurrently to the longitudinal and transverse directions in the fifth embodiment, the measurement of length is performed more easily. In addition since there are provided four illuminating optical systems, the intensity of illuminating light is increased much more.

Figure 18:
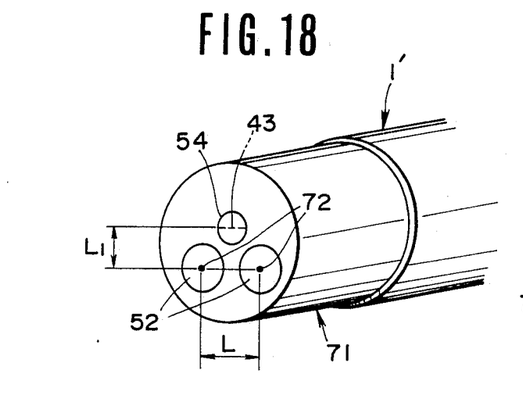
FIG. 18 is a perspective view of the sixth embodiment according to this invention.

FIG. 18 illustrates the sixth embodiment of this invention.

Length-measuring optical adaptor 71 according to said sixth embodiment is provided with spot index 72, 72 to the projecting optical systems 52, 52 in lieu of linear indexes 53, 53 for the length-measuring optical adaptor 51 as shown in FIG. 11. A datum index 43 is provided to eyepiece member 4 as shown in FIG. 8. This datum index 43 is positioned so as to pass the centre of visual field and in parallel to the plane including the optical axes of projecting optical systems 52, 52 spaced apart by a distance of L with respect to each other and so that the distance from the datum index 43 to the plane is equal to a constant datun length of $L_1$.

Figure 19:
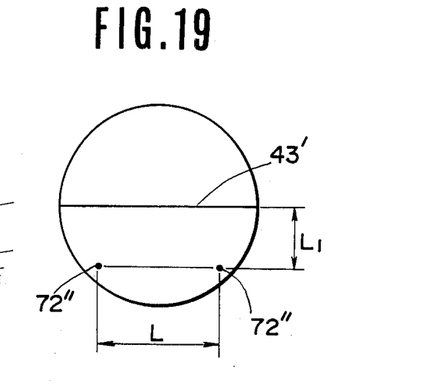
FIG. 19 is a schematic view showing the image of the index observed through the eyepiece member and FIG. 20 is a schematic view illustrating the image of the index observed through the eyepiece member when the projecting light is projected on an object present farther from the adaptor than the object of FIG. 19.
Figure 20:
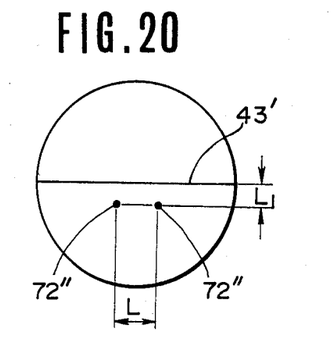

Accordingly, within the visual field observed through the eyepiece member when the indexes are projected on a plane nearer or further from the leading end of adaptor, images of indexes 72", 72" are developed. The distance between the two images corresponds to datum length L and the distance to the image of datum index 43' corresponds to datum length $L_1$ as shown in FIGS. 19 and 20, respectively.

According to the sixth embodiment, datum lengths $L_1$ and L are displayed concurrently to the longitudinal and transverse directions and since there is provided no limitation in the rotational directions of indexes 72, 72 attached to projecting optical systems 52, 52 or no requirement for arranging two indexes 72, 72 precisely in parallel to each other, such conditions are preferable in the assembly of adaptor.

Furthermore, it is possible to set $L-L_1$ by setting the positional relation of projecting optical systems 52, 52 and visual field-changing optical system 54.

Figure 21:
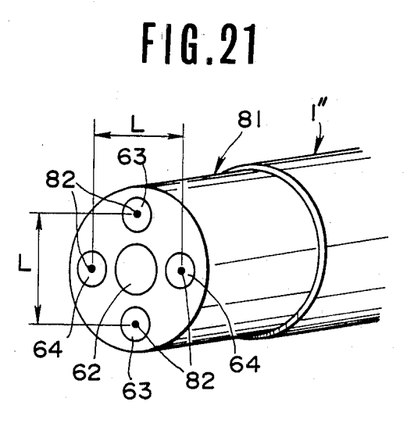
FIG. 21 is a perspective view of the seventh embodiment.

FIG. 21 illustrates the seventh embodiment of this invention.

Figure 22:
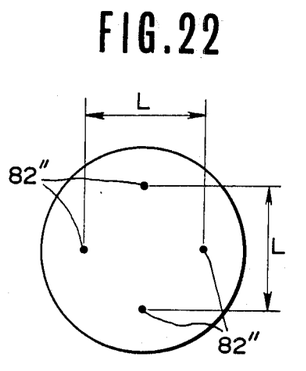
FIG. 22 is a schematic view illustrating the image of the index observed through the eyepiece member and FIG. 23 is a schematic view illustrating the image of the index observed through the eyepiece member when the projecting light is projected on an object present farther from the adaptor than the object shown in FIG. 22.
Figure 23:
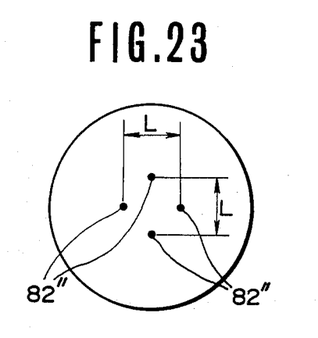

Length-measuring optical adaptor 81 according to the seventh embodiment is provided with four spot indexes 82, 82, 82, 82 on the optical axes of projecting optical systems 63, 63; 64, 64 in lieu of linear indexes 65, 65; 66, 66 on projecting optical systems 63, 63; 64, 64 shown in FIG. 15. The distances between the two sets of confronted indexes 82, 82 are kept in a constant datum length L. Accordingly, when the images projected on a plane nearer or further from the leading end of adaptor are observed, the images of indexes 82", 82", 82", 82" are observed respectively as shown in FIGS. 22 and 23. The distances between two sets of confronted images 82", 82" are equal to datum length L.

The seventh embodiment has an effect substantially similar to that of the sixth embodiment. In addition, four illuminating optical systems are employed so as to increase the intensity of illuminating light.

In addition, endoscope 1, 1', 1" applied with an adaptor according to any embodiment is not limited to a flexible type employing fibre bundle(s) for forming the image guide(s) 15 as image transmitting means but may be a rigid type endoscope employing optical relay system(s). It may be flexible or rigid type employing solid pick-up element(s) such as charge-coupled device, BBD or the like.

Moreover in each of above-mentioned embodiments, visual field-changing optical system 22, 32, 54, 62 includes that changing the angle of visual field of objective optical system 14 only in the main body of endoscope and that changing the direction of visual field. The present invention includes an adaptor designed to measure the length by projecting a length-measuring index at the same angle of field without changing the angle of the field.

Moreover, as length measuring indexes, there have been disclosed linear, circular and spot indexes, but the index may be formed otherwise. Moreover, the index may be provided on a lens member of the projecting optical system, glass plate or glass rod and displayed with a discriminating color such as green or blue in the observation of body cavity. When a plural number of indexes are projected on a plane, they can be displayed by different colors.

Still further, in length-measuring optical adaptors 21, 31, ..., 81 disclosed, the body of the length-measuring optical adaptor may not be formed integrally but may be formed in two pieces so that, for example, the part forming the index may be attached detachably to the main body of adaptor so that when the part is detached, the adaptor is used as an optical adaptor having no index-projection means but the angle of field or direction of visual field may be changed and when the part is attached, the adaptor is used as a length-measuring optical adaptor.

Still further, when the adaptor according to this invention is not attached and the endoscope has stepped tip member 8 having possibility of injuring the inner wall of body cavity during the insertion or the like, a cover member of substantially ring form may be fitted to eliminate the stepped portion.

Still further, although the above-mentioned embodiments do not have an instrumental channel, for an insert member equipped with an instrumental channel, an additional through-hole connected to the channel may be provided.

Still further, this invention, includes any combination of above-mentioned embodiments. For example, the adaptors according to the first and second embodiments can be combined to be used for the same endoscope 1.

Still further, the objective optical system and single or plurality of illuminating optical system(s) are not limited to those mentioned hereinabove.

As set further hereinbefore, this invention provides an optical adaptor for measuring length of an object viewed by incorporating an optical adaptor capable to be attached detachably to the insert member of an endoscope with an index or indexes, thereby displaying a datum length by projecting the index(s) on the surface of object to be observed so as to change the visual direction or the angle of field only be exchanging another optical adaptor for measuring the length without degrading the measuring function to extend the applications of optical adaptor economically.

Moreover, when such function for measuring the length is not required, the endoscope can be employed as an ordinary endoscope without losing the light intensity by detaching the optical adaptor economically.

Moreover, when such function for measuring the length is not required, the endoscope can be employed as an ordinary endoscope without losing the light intensity by detaching the optical adaptor.

Still further, it is apparent that different embodiments based on this invention can be thought of within a wide range without departing from the spirit and scope of this invention. Hence this invention is not restricted to any particular embodiments except the limitation as claimed by the attached claims.

What is claimed is:

1. An optical adaptor for measuring length of an object viewed to be attached to an endoscope, the endoscope comprising: an elongated insert member capable of being inserted through a body cavity; a handle member connected to a trailing end of said insert member; an illuminating optical system arranged at a tip portion of said insert member; an objective optical member arranged at the tip portion of said insert member adjacently to said illuminating optical system, said objective optical member for imaging the object illuminated by said illuminating optical system; and observation means for observing the object from the handle member side by transmitting the image from said objective optical system to said handle member side; the adaptor comprising a body, attaching means including a bore in said body for receiving detachably a tip portion of said insert member, a projecting optical system arranged in said adaptor so that when said adaptor is attached to said tip portion said projecting optical system is attached to said illuminating optical system in a confronting relation with said illuminating optical system, a view field-changing optical system arranged in said adaptor so that when said adaptor is attached to said tip portion said view field-changing optical system is attached to said objective optical system in a confronting relation with said objective optical system, and at least one index attached to said projecting optical system to be projected on the object through said projecting optical system for providing a datum length.

2. An adaptor of direct view type according to claim 1 wherein said projecting and view field-changing optical systems are positioned on extended optical axes of said illuminating and objective optical systems of said endoscope.

3. An adaptor of side view type according to claim 1 wherein an optical axis of said projecting optical system is bent in a direction perpendicular to an optical axis of said illuminating optical system and an optical axis of said view field-changing optical system is bent in a direction perpendicular to an optical axis of said objective optical system.

4. An adaptor according to claim 1 wherein said at least one index is arcuated around the optical axis of said projecting optical system to be projected at an angle equal to the angle of field of said view field-changing optical system.

5. An adaptor according to claim 1 wherein said at least one index is a plurality of indexes formed into spots on respective optical axes of a plurality of projecting optical systems.

6. An adaptor according to claim 1 wherein said at least one index comprises a pair of straight segments passing the respective optical axes of a plurality of projecting optical systems in parallel relation to each other.

7. An adaptor according to claim 1 wherein said at least one index comprises a straight segment crossed with the optical axis of projecting optical system and perpendicular to a plane including the optical axes of said view field-changing and projecting optical systems.

* * * * *